United States Patent
Bleier

(10) Patent No.: US 12,295,933 B2
(45) Date of Patent: May 13, 2025

(54) METHODS AND COMPOSITIONS TO TREAT AND DIAGNOSE DISEASES OR PATHOLOGIES ASSOCIATED WITH INFLAMMATION OF THE SINUSES AND NASAL CAVITY

(71) Applicant: Massachusetts Eye and Ear Infirmary, Boston, MA (US)

(72) Inventor: Benjamin S. Bleier, Weston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 869 days.

(21) Appl. No.: 17/442,730

(22) PCT Filed: Mar. 24, 2020

(86) PCT No.: PCT/US2020/024476
§ 371 (c)(1),
(2) Date: Sep. 24, 2021

(87) PCT Pub. No.: WO2020/198232
PCT Pub. Date: Oct. 1, 2020

(65) Prior Publication Data
US 2022/0168260 A1    Jun. 2, 2022

Related U.S. Application Data

(60) Provisional application No. 62/823,233, filed on Mar. 25, 2019.

(51) Int. Cl.
| A61K 31/277 | (2006.01) |
| A61K 9/00 | (2006.01) |
| A61K 45/06 | (2006.01) |
| A61P 11/02 | (2006.01) |

(52) U.S. Cl.
CPC .......... *A61K 31/277* (2013.01); *A61K 9/0043* (2013.01); *A61K 45/06* (2013.01); *A61P 11/02* (2018.01)

(58) Field of Classification Search
CPC .............................. A61K 31/277; A61P 11/02
See application file for complete search history.

(56) References Cited

U.S. PATENT DOCUMENTS

| 1,603,758 A | 10/1926 | Fisher |
| 1,856,811 A | 5/1932 | Inaki |
| 2,989,437 A | 6/1961 | Wruble et al. |
| 3,847,145 A | 11/1974 | Grossan |
| 4,444,879 A | 4/1984 | Foster et al. |
| 5,045,694 A | 9/1991 | Beavis et al. |
| 5,118,937 A | 6/1992 | Hillenkamp et al. |
| 5,420,016 A | 5/1995 | Boguslaski et al. |
| 5,649,530 A | 7/1997 | Ballini |
| 5,719,060 A | 2/1998 | Hutchens et al. |
| 5,898,037 A | 4/1999 | Marx |
| 6,225,047 B1 | 5/2001 | Hutchens et al. |
| 6,267,980 B1 | 7/2001 | Gilbert et al. |
| 6,328,718 B1 | 12/2001 | Chiang et al. |
| 6,451,815 B1 | 9/2002 | Hwang et al. |
| 6,468,798 B1 | 10/2002 | Debs et al. |
| 6,503,953 B2 | 1/2003 | Vyden |
| 6,520,284 B2 | 2/2003 | Spannbauer et al. |
| 6,579,898 B2 | 6/2003 | Humphrey |
| 6,736,792 B1 | 5/2004 | Liu |
| 6,907,879 B2 | 6/2005 | Drinan et al. |
| 6,924,153 B1 | 8/2005 | Boehringer et al. |
| 7,115,565 B2 | 10/2006 | Gao et al. |
| 7,544,192 B2 | 6/2009 | Eaton et al. |
| 7,820,681 B1 | 10/2010 | Davis |
| 7,888,049 B2 | 2/2011 | Shaari |
| 7,935,731 B2 | 5/2011 | Davis |
| 8,003,106 B2 | 8/2011 | Mikayama et al. |
| 8,124,091 B2 | 2/2012 | Kato et al. |
| 8,162,921 B2 | 4/2012 | Flickinger et al. |
| 8,337,454 B2 | 12/2012 | Eaton et al. |
| 8,357,696 B2 | 1/2013 | Surber et al. |
| 8,637,469 B2 | 1/2014 | Levitt |
| 8,980,848 B2 | 3/2015 | Chan et al. |
| 9,744,210 B2 * | 8/2017 | Bleier ................. A61K 31/545 |
| 10,653,745 B2 | 5/2020 | Bleier |
| 11,007,246 B2 * | 5/2021 | Bleier ................. A61K 31/473 |
| 11,786,574 B2 * | 10/2023 | Bleier .................... A61K 45/06 514/171 |
| 2002/0177147 A1 | 11/2002 | Mealey et al. |
| 2003/0180815 A1 | 9/2003 | Rawson et al. |
| 2004/0166110 A1 | 8/2004 | Mechetner et al. |
| 2005/0186144 A1 | 8/2005 | Bloom et al. |
| 2005/0245906 A1 | 11/2005 | Makower et al. |
| 2006/0051300 A1 | 3/2006 | Chaudry |

(Continued)

FOREIGN PATENT DOCUMENTS

| CN | 101380328 | 3/2009 |
| WO | WO 2001/058470 | 8/2001 |
| WO | WO 2005/072704 | 8/2005 |
| WO | WO 2006/051206 | 5/2006 |
| WO | WO 2008/058160 | 5/2008 |
| WO | WO 2009/140715 | 11/2009 |
| WO | WO 2012/006599 | 1/2012 |
| WO | WO 2014/106021 | 7/2014 |
| WO | WO 2017/123933 | 7/2017 |
| WO | WO 2019/139901 | 7/2019 |

OTHER PUBLICATIONS

Extended European Search Report in European Appln. No. 21827979.2, dated Jun. 3, 2024, 7 pages.
Chevalier et al., "Proteomic Studies of Saliva: A Proposal for a Standardized Handling of Clinical Samples," Clin Proteom, Oct. 2007, 3:13-21.
Drewe et al., "HIV protease inhibitor ritonavir: a more potent inhibitor of P-glycoprotein than the cyclosporine analog SDZ PSC 833," Biochemical Pharmacology, May 1999, 57(10):1147-1152.
Laberge et al., "P-glycoprotein (ABCB1) modulates collateral sensitivity of a multidrug resistant cell line to verapamil," Archives of Biochemistry and Biophysics, Nov. 2009, 491(1-2):53-60.

(Continued)

*Primary Examiner* — Golam M Shameem
(74) *Attorney, Agent, or Firm* — Fish & Richardson P.C.

(57) ABSTRACT

Methods and compositions for the treatment of rhinosinusitis in a subject using topical verapamil.

20 Claims, No Drawings

(56) References Cited

U.S. PATENT DOCUMENTS

| | | |
|---|---|---|
| 2006/0134009 A1 | 6/2006 | Deaver et al. |
| 2006/0275920 A1 | 12/2006 | Petrilla et al. |
| 2006/0276743 A1 | 12/2006 | MacMahon et al. |
| 2007/0009533 A1 | 1/2007 | Sikic et al. |
| 2007/0015719 A1 | 1/2007 | Jenkins et al. |
| 2007/0020299 A1 | 1/2007 | Pipkin et al. |
| 2007/0105237 A1 | 5/2007 | Corstjens et al. |
| 2007/0178526 A1 | 8/2007 | Kountakis et al. |
| 2007/0226012 A1 | 9/2007 | Salgado et al. |
| 2008/0081341 A1 | 4/2008 | Maher et al. |
| 2008/0118925 A1 | 5/2008 | Cuppens et al. |
| 2008/0152640 A1 | 6/2008 | Prehm |
| 2008/0160538 A1 | 7/2008 | Saul et al. |
| 2008/0199522 A1 | 8/2008 | Sawada et al. |
| 2008/0221507 A1 | 9/2008 | Hoke et al. |
| 2009/0202665 A1 | 8/2009 | Javer et al. |
| 2009/0246886 A1 | 10/2009 | Buck |
| 2010/0016267 A1 | 1/2010 | Theeuwes et al. |
| 2010/0024530 A1 | 2/2010 | Hopkins |
| 2010/0129316 A1 | 5/2010 | Levitt |
| 2010/0285610 A1 | 11/2010 | Saul et al. |
| 2011/0020457 A1 | 1/2011 | Panyam et al. |
| 2011/0118199 A1 | 5/2011 | Dormeyer |
| 2011/0240012 A1 | 10/2011 | Pilon |
| 2012/0034229 A1 | 2/2012 | Rousselle et al. |
| 2012/0095019 A1 | 4/2012 | Sinba et al. |
| 2012/0219565 A1 | 8/2012 | Presta |
| 2012/0240930 A1 | 9/2012 | Kristensson et al. |
| 2013/0059399 A9 | 3/2013 | Saul et al. |
| 2013/0071335 A1 | 3/2013 | Lasser |
| 2013/0189794 A1 | 7/2013 | Emeric et al. |
| 2013/0295691 A1 | 11/2013 | Saul |
| 2014/0093880 A1 | 4/2014 | Kim et al. |
| 2014/0206100 A1 | 7/2014 | Saul |
| 2014/0336463 A1 | 11/2014 | Shikani |
| 2014/0370616 A1 | 12/2014 | Gupta et al. |
| 2015/0017099 A1 | 1/2015 | Cohen et al. |
| 2016/0193286 A1 | 7/2016 | Bleier |
| 2016/0228502 A1 | 8/2016 | Desmond et al. |
| 2016/0245808 A1 | 8/2016 | Faustman |
| 2017/0128659 A1 | 5/2017 | Mehta |
| 2017/0348384 A1 | 12/2017 | Bleier |
| 2018/0104253 A1 | 4/2018 | Yadidi et al. |
| 2019/0086426 A1 | 3/2019 | Bleier et al. |
| 2020/0197481 A1 | 6/2020 | Bleier |
| 2021/0330737 A1 | 10/2021 | Bleier |
| 2023/0226008 A1 | 7/2023 | Bleier et al. |
| 2024/0148823 A1 | 5/2024 | Bleier |

OTHER PUBLICATIONS

Shin et al., "The effect of nasal polyp epithelial cells on eosinophil activation," Laryngoscope, Aug. 2003, 113:1374-7.

Yamaguchi et al., "Disposable collection kit for rapid and reliable collection of saliva," American Journal of Human Biology, Sep.-Oct. 2015, 27(5):720-723.

Derendorf et al., "Molecular and clinical pharmacology of intranasal corticosteroids: clinical and therapeutic implications," Allergy, Oct. 2008, 63(10):1292-300.

Desrosiers et al., "Canadian clinical practice guidelines for acute and chronic rhinosinusitis," J Otolaryngol Head Neck Surg., May 2011, 40 Suppl 2:S99-193, 38 pages.

Douglas et al., "Phase 1 Clinical Study to Assess the Safety of a Novel Drug Delivery System Providing Long-Term Topical Steroid Therapy for Chronic Rhinosinusitis," International Forum of Allergy & Rhinology, Apr. 2019, 9(4):378-87.

Farrell et al., "High multidrug resistance (P-glycoprotein 170) expression in inflammatory bowel disease patients who fail medical therapy," Gastroenterology, Feb. 2000, 118(2):279-88.

Forwith et al., "Advance: a multisite trial of bioabsorbable steroid-eluting sinus implants," Laryngoscope, Nov. 2011, 121(11):2473-80.

Gurrola and Borish, "Chronic rhinosinusitis: Endotypes, biomarkers, and treatment response," J Allergy Clin Immunol., Dec. 2017, 140(6):1499-508.

International Search Report & Written Opinion in International Appln. No. PCT/US2021/038281, mailed Sep. 29, 2021, 9 pages.

Mares-Sámano et al., "Abstract: Identification of putative steroid-binding sites in human ABCB1 and ABCG2," Eur J Med Chem., Sep. 2009, 44(9):3601-11, 1 page.

Rosenfeld et al., "Clinical practice guideline (update): adult sinusitis," Otolaryngol Head Neck Surg., Apr. 2015, 152(2 Suppl):S1-39.

Scadding et al., "BSACI guidelines for the management of rhinosinusitis and nasal polyposis," Clin Exp Allergy, Feb. 2008, 38(2):260-75.

Sindwani et al., "Navigate I: Randomized, Placebo-Controlled, Double-Blind Trial of the Exhalation Delivery System With Fluticasone for Chronic Rhinosinusitis With Nasal Polyps," Am J Rhinol Allergy, Jan. 2019, 33(1):69-82.

Szefler, "Pharmacokinetics of intranasal corticosteroids," J Allergy Clin Immunol., Jul. 2001, 108(1 Suppl):S26-31.

Webster and Carlstedt-Duke, "Abstract: Involvement of multidrug resistance proteins (MDR) in the modulation of glucocorticoid response," J Steroid Biochem Mol Biol., Nov. 2002, 82(4-5):277-88, 1 page.

Office Action in Chinese Appln. No. 202180051224.3, mailed on Oct. 11, 2024, 18 pages (with English translation).

Abdel Mouez et al., "Bioavailability enhancement of verapamil HCI via intranasal chitosan microspheres," Eur. J. Pharm. Sci., 2014, 51:59-66.

Akdis et al., "Endotypes and phenotypes of chronic rhinosinusitis: a Practall document of the European Academy of Allergy and Clinical Immunology and the American Academy of Allergy, Asthma & Immunology," J Allergy Clin Immunol, 2013, 131(6):1479-90.

Al-Massarani et al., "In vitro Cytotoxic, Antibacterial and Antiviral Activities of Triterpenes from the Red Sea Sponge, *Siphonochalina siphonella*," Tropical Journal of Pharmaceutical Research, Jan. 2015. 14(1):33-40.

Amin, "P-glycoprotein Inhibition for Optimal Drug Delivery," Drug Target Insights, 2013, 7:27-34.

Amorim et al., "Nasal eosinophilia: an indicator of eosinophilic inflammation in asthma," Clin Exp Allergy, Jun. 2010; 40(6):867-874.

Anderson, "The Clinical Plasma Proteome: A Survey of Clinical Assays for Proteins in Plasma and Serum." Clinical Chemistry, 2010, 56(2):177-185.

Aqil et al., "Antimicrobial, antioxidant, and antimutagenic activities of selected marine natural products and tobacco cembranoids," Drug and Chemical Toxicology, 2011, 34(2):167-179.

Arnold et al., "Pharmacodynamics of acute intranasal administration of verapamil: comparison with i.v. and oral administration," Biopharm. Drug Dispos, 1985, 6(4):447-54.

Bachert et al., "Effect of Subcutaneous Dupilumab on Nasal Polyp Burden in Patients With Chronic Sinusitis and Nasal Polyposis: A Randomized Clinical Trial," JAMA, Feb. 2016, 315(5):469-79.

Bachert et al., "*Staphylococcus aureus* enterotoxins: a key in airway disease?" Allergy, Jun. 2002:57(6):480-7.

Bark et al., "PSC833, cyclosporine analogue, downregulates MORI expression by activating JNK/c-Jun/AP-1 and suppressing NF-kB," Cancer Chemother Pharmacol., May 2010, 65(6):1131-1136.

Bebawy et al., "Membrane microparticles mediate transfer of P-glycoprotein to drug sensitive cancer cells," Leukemia, 2009, 23:1643-1649.

Becker, "Cluster headache: a conventional pharmacological management," Headache, Jun. 2013, 53(7):1191-1196.

Blackwell et al., "Summary health statistics for U.S. adults: National Health Interview Survey, 1997," Vital Health Stat 10, May 2002. (205):1-109.

Bleier & Feldman, "Corticosteroid Sensitivity of Epithelial MDR. I/P-gp in Chronic Sinusitis with Nasal Polyps," Abstract of Presentation at Proceedings of the 58th Annual Meeting of the American Rhinologic Society, Washington, DC, Sep. 8, 2012, p. 32, 2 pages.

Bleier et al., "Chitosan glycerophosphate-based semirigid dexamethasone eluting biodegradable stent," Am J Rhinol Allergy, 2009, 23:76-79.

(56) References Cited

OTHER PUBLICATIONS

Bleier et al., "P-glycoprotein functions as an immunomodulator in healthy human primary nasal epithelial cells," Int Forum Allergy Rhinol, 2013, 3 (6):433-8, 6 pages.
Bleier et al., "P-glycoprotein promotes epithelial T helper 2-associated cytokine secretion in chronic sinusitis with nasal polyps," Int Forum Allergy Rhinol, 2014, 4 (6):488-94.
Bleier et al., "P-glycoprotein regulates *Staphylococcus aureus* enterotoxin B-stimulated interleukin-5 and thymic stromal lymphopoietin secretion in organotypic mucosal explants," Int Forum Allergy Rhinol, 2016, 6(2):169-77.
Bleier et al., "Primary human sinonasal epithelial cell culture model for topical drug delivery in patients with chronic rhinosinusitis with nasal polyposis," J. Pharm. Pharmacol, 2012, 64:449-56.
Bleier et al., "Regional expression of epithelial MDRI/P-glycoprotein in chronic rhinosinusitis with and without nasal polyposis." Int Forum Allergy & Rhinol., Mar.-Apr. 2012;2(2): 122-125.
Bleier et al., "Verapamil modulates interleukin-5 and interleukin-6 secretion in organotypic human sinonasal polyp explants," Int Forum Allergy Rhinol, 2014, 5 (1):10-13.
Bleier, "P-glycoprotein and Epithelial Cell Function," Presented at Federation of Clinical Immunology Societies, San Diego, CA, 2015, 24 pages.
Bleier, "P-glycoprotein in Epithelial Cell Function," Federation of Clinical Immunology Societies, Scientific Program, San Diego, CA, 2015, p. 8.
Bleier, "Regional Expression of Epithelial MDRI/P-gp in Chronic Sinusitis with and without Nasal Polyposis," Abstract of Presentation at Proceedings of the 57th Annual Meeting of the American Rhinologic Society, San Francisco, CA. Sep. 10, 2011, p. 71-72, 3 pages.
Brody et al., "High-content affinity-based proteomics: unlocking protein biomarker discovery," Expert Rev. Mol. Diagn., 2010, 10(8):1013-1022.
CA Office Action in Canadian Appln. No. 2,928,035, dated Jun. 26, 2020, 4 pages.
Cervin et al., "Effects of long-term clarithromycin treatment on lavage-fluid markers of inflammation in chronic rhinosinusitis." Clinical Physiology and Functional Imaging, 2009, 29(2):136-142.
Chiampanichayakul et al., "Production of monoclonal antibodies to P-glycoprotein: its application in detection of soluble and surface P-glycoprotein of leukemia patients," Int J Hematol, 2010, 92 (2):326-33.
Chin et al., "Nasal polyposis: an inflammatory condition requiring effective anti-inflammatory treatment," Curr Opin Otolaryngol Head Neck Surg, 2013, 21(1):23-30.
Cho et al., "Impact of chronic rhinosinusitis and endoscopic sinus surgery on bone remodeling of the paranasal sinuses," Am J Rhinol, 2008, 22(5):537-541.
Chu et al., "Detection of soluble P-glycoprotein in culture media and extracellular fluids," Biochem Biophys Res Commun, 1994, 203 (1):506-12.
Cleves and Kelly, "Protein translocation: Rehearsing the ABCs," Curr. Biol, 1996, 6:276-8.
ClinicalTrials.gov [online], "Trial of Topical Verapamil in Chronic Rhinosinusitis With Nasal Polyps," NCT03102190, Apr. 5, 2017, retrieved May 9, 2020, retrieved from URL <https://clinicaltrials.gov/ct2/show/NCT03102190>, 9 pages.
Cohen et al., "Electrocardiogramic abnormalities in patients with cluster headache on verapamil therapy," Neurology, 2007; 69(7):668-675.
Damm et al., "Proinflammatory effects of Staphylococcus aureus exotoxin B on nasal epithelial cells," Otolaryngol Head Neck Surg., 2006, 134(2):245-9.
Derycke et al., "Mixed T helper cell signatures in chronic rhinosinusitis with and without polyps," PLoS One, Jun. 2014, 9(6):e97581, 8 pages.
Detwiller et al., "Steroid-independent upregulation of matrix metalloproteinase 9 in chronic rhinosinusitis patients with radiographic evidence of osteitis," Int Forum Allergy Rhinol., May 2013, 3(5):364-368.
Di Noto et al., "Immunoglobulin free light chains and GAGs mediate multiple myeloma extracellular vesicles uptake and secondary NfkB nuclear translocation," Frontiers in Immunology, Oct. 2014, 5: Article 517, 15 pages.
Dinis et al., "Sinus tissue concentration of moxifloxacin after a single oral dose," Ann. Otol. Rhinol. Laryngol., 2004, 113(2):142-146.
Drach et al., "Involvement of P-glycoprotein in the transmembrane transport of interleukin-2 (IL-2), IL-4, and interferon-gamma in normal human T lymphocytes," Blood, Sep. 1996, 88(5):1747-54.
Drori et al., "Potentiation of anticancer-drug cytotoxicity by multidrug-resistance chemosensitizers involves alterations in membrane fluidity leading to increased membrane permeability," Eur J Biochem., Mar. 1995, 228:1020-9.
Edmiston et al., "Tissue and fluid penetration of garenoxacin in surgical patients," Surg. Infect. (Larchmt)., Apr. 2007, 8(2):179-88.
Ehrhardt et al., "16HBE140-human bronchial epithelial cell layers express P-glycoprotein, lung resistance-related protein, and caveolin-1," Pharm. Res. Apr. 2003; 20(4):545-51.
Erbek et al., "The role of allergy in the severity of nasal polyposis," Am J Rhinol, 2007, 21(6):686-90.
European Search Report in Application No. 13866961.9, dated Jun. 6, 2016, 7 pages.
Feldman et al., "P-glycoprotein is a marker of tissue eosinophilia and radiographic inflammation in chronic rhinosinusitis without nasal polyps." Int Forum Allergy Rhinol, 2013, 3 (8):684-7.
Ferguson, "Categorization of eosinophilic chronic rhinosinusitis," Curr Opin Otolaryngol Head Neck Surg., 2004, 12(3):237-242.
Fernandez et al., "Influence of the pro-inflammatory cytokines on P-glycoprotein expression and functionality," J Pharm. Pharm. Sci. Nov. 17, 2004: 7(3):359-71.
Fokkens et al., "EPOS 2012: European position paper on rhinosinusitis and nasal polyps 2012. A summary for otorhinolaryngologists," Rhinology, 2012, 50(1):1-12.
Fokkens et al., "European Position Paper on Rhinosinusitis and Nasal Polyps 2012," Rhinol Suppl. 2012. (23):3 p preceding table of contents, 1-298, 329 pages.
Gehanno et al., "A prospective, multicentre study of moxifloxacin concentrations in the sinus mucosa tissue of patients undergoing elective surgery of the sinus," J. Antimicrob. Chemother., May 2002, 49(5):821-826.
Georgalas et al., "Global Osteitis Scoring Scale and chronic rhinosinusitis: a marker of revision surgery," Clin Otolaryngol, 2010, 35(6):455-461.
Georgalas, "Osteitis and paranasal sinus inflammation: what we know and what we do not," Curr Opin Otolaryngol Head Neck Surg, Feb. 2013, 21(1):45-49.
Gevaert et al., "Mepolizumab, a humanized anti-IL-5 mAb, as a treatment option for severe nasal polyposis." J. Allergy Clin. Immunol., Nov. 2011, 128(5):989-95, 15 pages.
Gevaert et al., "Nasal IL-5 levels determine the response to anti-IL-S treatment in patients with nasal polyps," J. Allergy Clin, Immunol., Nov. 2006, 118(5):1133-41.
Golden et al., "Blood-brain barrier efflux transport," J Pharm Sci., Sep. 2003, 92(9):1739-53.
Gong et al., "Microparticles and their emerging role in cancer multidrug resistance," Cancer Treatment Reviews, 2012, 38: 226-234.
Gudis et al., "Acquired cilia dysfunction in chronic rhinosinusitis," Am. J. Rhinol. Allergy, 26:1-6.
Han et al., "Predictors of bronchial hyperresponsiveness in chronic rhinosinusitis with nasal polyp," Allergy, Jan. 2009, 64(1):118-22.
Harding et al., "Receptor-mediated Endocytosis of Transferrin and of the Transferrin Receptor in Rat Reticulocytes Recycling," The Journal of Cell Biology, Aug. 1983, 97: 329-339.
Harvey et al., "Fluid residuals and drug exposure in nasal irrigation," Otolaryngol. Head Neck Surg., Dec. 2009, 141(6):757-761.

(56) References Cited

OTHER PUBLICATIONS

Hashemi et al., "Effectiveness of itraconazole on clinical symptoms and radiologic findings in patients with recurrent chronic rhinosinusitis and nasal polyposis," Adv. Biomed. Res., 2014, 3(162): 5 pages.

Hashioka et al., "Inhibition of human astrocyte and microglia neurotoxicity by calcium channel blockers," Neuropharmacology, Sep. 2012, 63(4):685-691.

Hedman et al., "Prevalence of asthma, aspirin intolerance, nasal polyposis and chronic obstructive pulmonary disease in a population-based study," Int. J. Epidemiol., Aug. 1999, 28(4):717-22.

Henrique et al., "Epigenetic regulation of MDRI gene through post-translational histone modifications in prostate cancer," BMC Genomics, 2013, 14:898, 12 pages.

Hissaria et al., "Short course of systemic corticosteroids in sinonasal polyposis: a double-blind, randomized, placebo-controlled trial with evaluation of outcome measures," J. Allergy Clin Immunol., Jul. 2006, 118(1):128-33.

Hopkins et al., "Long-term outcomes from the english national comparative audit of surgery for nasal polyposis and chronic rhinosinusitis," Laryngoscope, Dec. 2009, 119(12):2459-2465.

Hopkins et al., "Psychometric validity of the 22-item Sinonasal Outcome Test," Clin Otolaryngol, 2009. 34:447-454.

Hopkins et al., "The Lund-Mackay staging system for chronic rhinosinusitis: how is it used and what does it predict?," Otolaryngol Head Neck Surg., 2007, 137(4):555-61.

Hospira GEHS, "Verpamil Hydrochloride Injection: Safety Data Sheet," Hospira Inc., revised Jun. 2014, 7 pages.

Hsiao et al., "National Ambulatory Medical Care Survey: 2007 summary," Natl. Health Stat. Report., Nov. 2010, 3(27):1-32.

Hu et al., "Release of Luminal Exosomes Contributes to TLR4-Mediated Epithelial Antimicrobial Defense," PLOS Pathogens, Apr. 2013, 9: e1003261, 14 pages.

International Preliminary Report on Patentability in International Application No. PCT/US2013/077945, mailed Jul. 9, 2015, 6 pages.

International Preliminary Report on Patentability in International Application No. PCT/US2017/013418, dated Jul. 17, 2018, 9 pages.

International Search Report and Written Opinion in International Application No. PCT/US2013/077945, mailed Apr. 29, 2014, 7 pages.

International Search Report and Written Opinion in International Application No. PCT/US2017/013418, mailed on Apr. 4, 2017, 16 pages.

International Search Report and Written Opinion in International Appln. No. PCT/US2020/024476, dated Jun. 11, 2020, 10 pages.

Iqbal et al., "Corticosteroid regulation of P-glycoprotein in the developing blood-brain barrier," Endocrinology, Mar. 2011, 152(3):1067-79.

Jain et al., "Reversal of P-Glycoprotein-Mediated Multidrug Resistance by Sipholane Triterpenoids," Journal of Natural Products, 2007, 70:928-931.

Jansen et al., "Exosomal Secretion of Cytoplasmic Prostate Cancer Xenograft-derived Proteins," Molecular & Cellular Proteomics, 2009, 8: 1192-1205.

Johansson et al., "Prevalence of nasal polyps in adults: the Skovde population-based study," Ann. Otol. Rhinol. Laryngol., Jul. 2003, 112(7):625-9.

Johnstone et al., "Reticulocyte Maturation and Exosome Release: Transferrin Receptor Containing Exosomes Shows Multiple Plasma Membrane Functions," Blood, 1989, 74: 1844-1851.

JP Office Action in Japanese Application No. 2018-536890, dated Dec. 8, 2020, 6 pages (with English translation).

JP Office Action in Japanese Application No. 2018-536890, dated Sep. 7, 2021, 4 pages (with English translation).

Kandimalla and Donovan, "Localization and differential activity of P-glycoprotein in the bovine olfactory and nasal respiratory mucosae," Pharm Res, 2005, 22 (7):1121-8.

Kato et al., "Serum exosomal P-glycoprotein is a potential marker to diagnose docetaxel resistance and select a taxoid for patients with prostate cancer," Urologic Oncology: Seminars and Original Investigations, 2015, 1-6, 6 pages.

Kern et al., "Perspectives on the etiology of chronic rhinosinusitis: An immune barrier hypothesis," Am J Rhinol, 2008, 22:549-559.

Khakzad et al., "Effect of verapamil on bronchial goblet cells of asthma: an experimental study on sensitized animals," Pulm. Pharmacol. Ther., Apr. 2012, 25(2):163-168.

Kharaziha et al., "Tumor cell-derived exosomes: A message in a bottle," Biochimica et Biophysica Acta, 2012, 1826: 103-111.

Kim et al., "Automated Heart-Type Fatty Acid-Binding Protein Assay for the Early Diagnosis of Acute Myocardial Infarction," Am J Clin Pathol, Jul. 2010,134:157-162.

Kirkeby et al., "Quantitative immunohistochemistry of fluorescence labelled probes using low-cost software," J Immunol. Methods, Jun. 2005, 301(1-2):102-13.

Klossek et al., "Prevalence of nasal polyposis in France: a cross-sectional, casecontrol study," Allergy, Feb. 2005, 60(2):233-7.

Kocharyan et al., "P-glycoprotein inhibition promotes prednisone retention in human sinonasal polyp explants," Int. Forum Allergy Rhinol., Aug. 2014, 4(9):734-738.

Kooij et al., "P-glycoprotein acts as an immunomodulator during neuroinflammation," PLoS One, Dec. 2009, 4(12):e8212.

Kopriva et al., "The anti-inflammatory effects of inhaled corticosteroids versus anti-leukotrienes on the lymphocyte P-glycoprotein (PGP) expression in asthmatic children," J Asthma., May 2009, 46(4):366-70.

Lalaker et al. "Chitin stimulates expression of acidic mammalian chitinase and eotaxin-3 by human sinonasal epithelial cells in vitro," Am J Rhinol Allergy, 2009, 23(1):8-14.

Lam et al., "Itraconazole and clarithromycin inhibit P-glycoprotein activity in primary human sinonasal epithelial cells," Int Forum Allergy Rhinol, 2015, 5(6):477-80, 4 pages.

Lane et al., "Altered expression of genes associated with innate immunity and inflammation in recalcitrant rhinosinusitis with polyps," Am J Rhinol., 2006, 20(2):138-44.

Lanteri-Minet et al., "Cardiac safety in cluster headache patients using the very high dose of verapamil (>720 mg/day)," J. Headache Pain, Apr. 2011, 12(2):173-176.

Lasser et al., "Exosomes in the nose induce immune cell trafficking and harbour an altered protein cargo in chronic airway inflammation," J. Transl. Med., Jun. 2016, 14(1)181, 14 pages.

Lee et al., "The incidence of concurrent osteitis in patients with chronic rhinosinusitis: a clinicopathological study," Am J Rhinol, 2006, 20(3):278-282.

Lee et al., "Exosomes and microvesicles: Extracellular vesicles for genetic information transfer and gene therapy," Hum. Mol. Genet, 2012, 21:125-134.

Lee et al., "Microvesicles as mediators of intercellular communication in cancer—the emerging science of cellular 'debris'," Semin. Immunopathol, 2011, 33: 455-467.

Lee et al., "Risk factors for protracted sinusitis in pediatrics after endoscopic sinus surgery," Auris Nasus Larynx., Dec. 2009, 36(6):655-60.

Levchenko et al., "Intercellular transfer of P-glycoprotein mediates acquired multidrug resistance in tumor cells," PNAS, 2005, 102:1933-1938.

Li et al., "Verapamil modulates LPS-induced cytokine production via inhibition of NF-kappa B activation in the liver, " Inflamm. Res., Mar. 2006, 55(3):108-13.

Lo Cicero et al., "Exosomes released by keratinocytes modulate melanocyte pigmentation," Nature Communications, 2015, 6: 7506, 8 pages.

Lopes-Rodrigues et al., "The network of P-glycoprotein and microRNAs interactions," Int. J. Cancer, 2014, 135(2):253-263.

Lopez and Martinez-Luis, "Marine Natural Products with P-Glycoprotein Inhibitor Properties," Mar Drugs, 2014, 12(1): 525-546.

Lund and Mackay, "Staging in rhinosinusitus," Rhinology, 1993, 31 (4):183-4.

Lv et al., "Exosomes mediate drug resistance transfer in MCF-7 breast cancer cells and a probable mechanism is delivery of P-glycoprotein," Tumor Biol, 2014, 35:10773-10779.

(56) References Cited

OTHER PUBLICATIONS

Mack et al., "Transfer of the chemokine receptor CCR5 between cells by membrane-derived microparticles: a mechanism for cellular human immunodeficiency virus 1 infection," Nat. Med, 2000, 6:769-775.
Mallegol et al., "T84-Intestinal Epithelial Exosomes Bear MHC Class II/Peptide Complexes Potentiating Antigen Presentation by Dendritic Cells," Gastroenterology, 2007, 132:1866-1876.
Marty et al., "ATP binding cassette transporter ABC1 is required for the release of interleukin-Ibeta by P2X7-stimulated and lipopolysaccharide-primed mouse Schwann cells," Glia, Mar. 2005, 49(4):511-9.
Matsumori et al., "Calcium Channel Blockers Differentially Modulate Cytokine Production by Peripheral Blood Mononuclear Cells," Circ. J., Mar. 2010, 74(3):567-571.
McCloy et al., "Partial inhibition of Cdk1 in G2 phase overrides the SAC and decouples mitotic events," Cell Cycle, 2014, 13 (9):1400-1412.
Meckes, Jr., "Exosomal Communication Goes Viral," Journal of Virology, 2015, 89: 5200-5203.
Mehta et al., "Blood and sputum eosinophil levels in asthma and their relationship to sinus computed tomographic findings," Mayo Clin Proc., Jun. 2008, 83(6):671-8.
Meltzer et al., "Development of questionnaires to measure patient preferences for intranasal corticosteroids in patients with allergic rhinitis," Otolaryngol. Head Neck Surg., Feb. 2005, 132(2):197-207.
Min et al., "Level of secreted HMGBI correlates with severity of inflammation in chronic rhinosinusitis," Laryngoscope, 2015, 125: E225-E230.
Miyake et al., "Double-blind placebo-controlled randomized clinical trial of verapamil for chronic rhinosinusitis with nasal polyps," J. Allergy Clin. Immunol., Jul. 2017, 140(1):271-273.
Mjösberg et al., "Human IL-25- and IL-33-responsive type 2 innate lymphoid cells are defined by expression of CRTH2 and CD161," Nat Immunol., Sep. 2011, 11;12(11):1055-62.
Morjani et al., "Immunosuppressors as multidrug resistance reversal agents," Methods Mol Biol., 2010. 596:433-46.
Munagala et al., "Synthesis and evaluation of Strychnos alkaloids as MDR reversal agents for cancer cell eradication," Bioorganic & Medicinal Chemistry, 2014, 22 (3):1148-1155.
Munoz et al., "Delivery of Functional Anti-miR-9 by Mesenchymal Stem Cell-derived Exosomes to Glioblastoma Multiforme Cells Conferred Chemosensitivity," Molecular Therapy—Nucleic Acids, 2013, 2(10):e126, 11 pages.
Nagarkar et al., "Thymic stromal lymphopoietin activity is increased in nasal polyps of patients with chronic rhinosinusitis," J. Allergy Clin. Immunol., Sep. 2013, 132(3):593-600.e12.
Newman et al., "Chronic sinusitis. Relationship of computed tomographic findings to allergy, asthma, and eosinophilia," JAMA, Feb. 1994, 271(5):363-7.
Nickel, "The mystery of nonclassical protein secretion. A current view on cargo proteins and potential export routes," Eur J Biochem., May 2003, 270(10):2109-19.
Nocera et al., "Exosomes mediate interepithelial transfer of functional P-glycoprotein in chronic rhinosinusitis with nasal polyps," The Laryngoscope, May 2017, 127(9):E295-E300, 6 pages.
Nocera et al., "Intact Soluble P-glycoprotein is Secreted by Sinonasal Epithelial Cells," Am. J. Rhinol. Allergy. 2016. 30(4):246-9.
Nocera et al., "Secreted P-Glycoprotein Is a Noninvasive Biomarker of Chronic Rhinosinusitis," The Laryngoscope, 2016, 4 pages.
Northwestern Medicine [online], "Nasal Saline Irrigation Instructions," Jun. 2018, retrieved May 11, 2020, 1 page.
Olze et al., "Eosinophilic nasal polyps are a rich source of cotaxin, cotaxin-2 and eotaxin-3," Rhinology, Jun. 2006, 44(2):145-50.
Orlandi et al., "International Consensus Statement on Allergy and Rhinology: Rhinosinusitis," Int. Forum Allergy Rhinol., Feb. 2016, 6 Suppl 1:S22-S209.

Palmeira et al., "Three Decades of P-gp Inhibitors: Skimming Through Several Generations and Scaffolds," Current Medicinal Chemistry, 2012, 19: 1946-2025.
Pan et al., "Electron Microscopic Evidence for Externalization of the Transferrin Receptor in Vesicular Form in Sheep Reticulocytes," The Journal of Cell Biology, 1985, 101: 942-948.
Pasquier et al., "Different modalities of intercellular membrane exchanges mediate cell-to-cell P-glycoprotein transfers in MCF-7 breast cancer cells," J. Biol. Chem, 2012, 287:7374-7387.
Pauwels et al., "Emerging biologics for the treatment of chronic rhinosinusitis," Expert Rev Clin Immunol, 2015, 11 (3):349-61.
Peric et al., "Effect of long-term, low-dose clarithromycin on T helper 2 cytokines, eosinophilic cationic protein and the 'regulated on activation, normal T cell expressed and secreted' chemokine in the nasal secretions of patients with nasal polyposis," J. Laryngol. Otol., May 2012, 126(5):495-502.
Peters et al., "Evidence for altered activity of the IL-6 pathway in chronic rhinosinusitis with nasal polyps," J Allergy Clin Immunol., Feb. 2010, 125(2):397-403.
Pfaffe et al., "Diagnostic Potential of Saliva: Current State and Future Applications," Clin. Chem., May 2011, 57(5):675-687.
Philips et al., "Rapid Point-Of-Care Breath Test for Biomarkers of Breast Cancer and Abnormal Mammograms," PLoS One, 2014, 9(3):e90226.
Piccirillo et al., "Psychometric and clinimetric validity of the 20-Item Sino-Nasal Outcome Test (SNOT-20)," Otolaryngol Head Neck Surg., 2002, 126(1):41-7.
Poetker et al.. "Oral corticosteroids in the management of adult chronic rhinosinusitis with and without nasal polyps: an evidence-based review with recommendations." Int. Forum Allergy Rhinol., Feb. 2013. 3(2):104-120, 17 pages.
Ponikau et al., "An immunologic test for chronic rhinosinusitis based on free intranasal eosinophilic major basic protein," Int Forum Allergy Rhinol, 2015, 5 (1):28-35.
Quintanilla-Dieck, et al., "Comparison of disease-specific quality-of-life instruments in the assessment of chronic rhinosinusitis," International Forum of Allergy & Rhinology, 2012, 2(6):437-443.
Rabinowits et al., "Exosomal MicroRNA: A Diagnostic Marker for Lung Cancer," Clinical Lung Cancer, 2009, 10: 42-46.
Rawal et al., "Post-operative budesonide irrigations for patients with polyposis: a blinded, randomized controlled trial," Rhinology, Sep. 2015, 53(3):227-34.
Reh et al., "Treatment-recalcitrant chronic rhinosinusitis with polyps is associated with altered epithelial cell expression of interleukin-33," Am J Rhinol Allergy, 2010, 24(2):105-9.
Riechelmann et al., "Biological markers in nasal secretions," Eur. Respir. J., Apr. 2003, 21(4):600-605.
Rosenfeld et al., "Clinical practice guideline: adult sinusitis," Otolaryngol Head Neck Surg., Sep. 2007, 137(3 Suppl):S1-31.
Rotenberg et al., "Postoperative care for Samter's triad patients undergoing endoscopic sinus surgery: a double-blinded, randomized controlled trial," Laryngoscope, Dec. 2011, 121(12):2702-5.
Rudmik et al., "Productivity costs in patients with refractory chronic rhinosinusitis," Laryngoscope, Sep. 2014, 124(9):2007-2012.
Ruocco et al., "A new collection method for the evaluation of nasal mucus proteins," Clin Exp Allergy, Jul. 1998, 28(7):881-888.
Rupa et al., "A prospective, randomised, placebo-controlled trial of postoperative oral steroid in allergic fungal sinusitis," Eur. Arch. Otorhinolaryngol., Feb. 2010, 267(3):233-8.
Ryan et al., "Correlations Between Symptoms, Nasal Endoscopy, and In-Office Computed Tomography in Post-Surgical Chronic Rhinosinusitis Patients," Laryngoscope, 2011, 121(3):674-678.
Sachse et al., "*Staphylococcus aureus* invades the epithelium in nasal polyposis and induces IL-6 in nasal epithelial cells in vitro," Allergy, Nov. 2010, 65(11):1430-7.
Sarangapani et al., "Interspecies dose extrapolation for inhaled dimethyl sulfate: a PBPK model-based analysis using nasal cavity N7-methylguanine adducts," Inhal, Toxicol., Aug. 2004, 16(9):593-605.
SBI System Biosciences, Exo-Glow™ Tracking Labels, 2014, 2 pages.
SBI System Biosciences, ExoQuick-TC™ Exosome Precipitation Solution—User Manual, 2013, 10 pages.

(56) References Cited

OTHER PUBLICATIONS

SBI System Biosciences, ExoQuick-TC™ Exosome precipitation, 2011, 2 pages.
SBI System Biosciences, ExoQuick™ Exosome Precipitation Solution—User Manual, 2013, 14 pages.
SBI System Biosciences, ExoQuick™M Exosome precipitation, 2011, 2 pages.
SBI System Biosciences, Exosome Antibodies, Array & Elisa Kits, 2014, 19 pages.
SBI System Biosciences, G-25 Spin column removal of ExoQuick polymers, downloaded from the internet on Jul. 3, 2015, presently available at https://www.systembio.com/wp-content/uploads/Remove-EXOQ-polymers.pdf. 1 page.
Scheffer et al., "Multidrug resistance related molecules in human and murine lung," J Clin Pathol, 2002. 55:332-339.
Schmid et al., "Released intranasal eosinophilic major basic protein as a diagnostic marker for polypoid chronic rhinosinusitis," Otolaryngol Head Neck Surg, 2010, 143 (3):386-91.
Schorey et al., "Exosomes and other extracellular vesicles in host-pathogen interactions," EMBO Rep, 2015. 16(1):24-43, 20 pages.
Secher et al., "Intranasal Verapamil in Allergen-Induced Rhinitis." Allergy, 1983, 38:565-570.
Shapiro et al., "Effect of quercetin on Hoechst 33342 transport by purified and reconstituted P-glycoprotein," Biochem Pharmacol., 1997, 53(4):587-96.
Sigma-Aldrich, Product Information: PKH26 Red Fluorescent Cell Linker Kits for General Cell Membrane Labeling, Technical Bulletin, Mar. 2011, 4 pages.
Smith et al., "Cost of adult chronic rhinosinusitis: A systematic review," Laryngoscope, Jul. 2015, 125(7)1547-56, 10 pages.
Smith et al., "National burden of antibiotic use for adult rhinosinusitis," J. Allergy Clin. Immunol., Nov. 2013, 132(5):1230-1232.
Snidvongs et al., "Correlation of the Kennedy Osteitis Score to clinico-histologic features of chronic rhinosinusitis," Int Forum Allergy Rhinol., May 2013, 3(5):369-75.
Snidvongs et al., "Osteitic bone: a surrogate marker of eosinophilia in chronic rhinosinusitis," Rhinology, Sep. 2012, 50(3):299-305.
Soler et al., "Impact of mucosal eosinophilia and nasal polyposis on quality-of-life outcomes after sinus surgery," Otolaryngol Head Neck Surg., Jan. 2010, 142(1):64-71.
Soler et al., "Relationship between clinical measures and histopathologic findings in chronic rhinosinusitis," Otolaryngol Head Neck Surg., Oct. 2009, 141(4):454-61.
Soudry et al., "Safety analysis of long-term budesonide nasal irrigations in patients with chronic rhinosinusitis post endoscopic sinus surgery," Int. Forum Allergy Rhinol., Jun. 2016, 6(6):568-72.
Stein et al., "Modulation of mdr1 expression by cytokines in human colon carcinoma cells: an approach for reversal of multidrug resistance," Br J Cancer, Nov. 1996, 74(9):1384-91.
Sun et al., "Clinical significance of eosinophilic cationic protein levels in nasal secretions of patients with nasal polyposis," Eur Arch Otorhinolaryngol., Jul. 2009, 266(7):981-6.
Szakács et al., "Targeting multidrug resistance in cancer," Nature Reviews, 2006, 5: 219-234.
Szucs et al., "Eosinophilia in the ethmoid mucosa and its relationship to the severity of inflammation in chronic rhinosinusitis," Am J Rhinol., 2002, 16(3):131-4.
Takeno et al., "Pathological mechanisms and clinical features of eosinophilic chronic rhinosinusitis in the Japanese population," Allergol Int., Sep. 2010, 59(3):247-56.
Taylor and Gercel-Taylor, MicroRNA signatures of tumor-derived exosomes as diagnostic biomarkers of ovarian cancer, Gynecologic Oncology, 2008, 110: 13-21.
Théry et al., "Isolation and characterization of exosomes from cell culture supernatants and biological fluids." Curr. Protoc. Cell Biol, 2006, Supplement 30: Unit 3.22.1-3.22.29.
Tomassen et al., "Inflammatory endotypes of chronic rhinosinusitis based on cluster analysis of biomarkers," J. Allergy Clin. Immunol, 2016, 137: 1449-1456.e4.

Torzewski et al., "Animal Models of C-Reactive Protein," Hindawl Publishing Corporation, Mediators of Inflammation, 2014, Article ID 683598, 1-7.
Tsuruo et al., "Enhancement of vincristine- and adriamycininduced cytotoxicity by verapamil in P388 leukemia and its sublines resistant to vincristine and adriamycin," Biochem. Pharmacol., Oct. 1982. 31(19):3138-40.
Vaidyanathan et al., "Treatment of chronic rbinosinusitis with nasal polyposis with oral steroids followed by topical steroids: a randomized trial," Ann. Intern. Med., Mar. 2011, 154(5):293-302, 12 pages.
Valadi et al., "Exosome-mediated transfer of mRNAs and microRNAs is a novel mechanism of genetic exchange between cells," Nature Cell Biology, 2007, 9: 654-659.
Van Crombruggen et al., "Pathogenesis of chronic rhinosinusitis: inflammation," J Allergy Clin Immunol., Oct. 2011, 128(4):728-32.
Van Der Vekiens et al., "Human and equine cardiovascular endocrinology: beware to compare," Cardiovascular Endocrinology, 2013, 2(4):67-76.
Van Deun et al., "The impact of disparate isolation methods for extracellular vesicles on downstream RNA profiling," Journal of Extracellular Vesicles, 2014, 3: 24858, 14 pages.
Van Niel et al., "Intestinal Epithelial Cells Secrete Exosome-like Vesicles," Gastroenterology, 2001, 121; 337-349.
Van Zele et al., "Differences in initial immunoprofiles between recurrent and nonrecurrent chronic rhinosinusitis with nasal polyps," Am. J. Rhinol. Allergy, 2014, 28(3): 192-8.
Van Zele et al., "Oral steroids and doxycycline: two different approaches to treat nasal polyps," J. Allergy Clin Immunol., May 2010, 125(5):1069-1076.e4.
Varma et al., "P-glycoprotein inhibitors and their screening: a perspective from bioavailability enhancement," Pharmacological Research, 2003, 48: 347-359.
Vogelgesang et al., "Stereoselective first-pass metabolism of highly cleared drugs: studies of the bioavailability of L- and D-verapamil examined with a stable isotope technique," Br. J. Clin. Pharmacol., Nov. 1984, 18(5):733-740.
Wallace et al., "The diagnosis and management of rhinitis: An updated practice parameter," J. Allergy Clin. Immunol., Aug. 2008, 122:S1-S84.
Walsh and Falsey, "A simple and reproducible method for collecting nasal secretions in frail elderly adults, for measurement of virus-specific IgA," J Infect Dis., May 1999, 179(5):1268-73.
Wanek et al., "A comparative small-animal PET evaluation of ["C]tariquidar, ["C]elacridar and (R)-["C]verapamil for detection of P-glycoprotein-expressing murine breast cancer." Eur J Nucl Med Mol Imaging., Jan. 2012, 39(1):149-159.
Watling et al., "Abstract: Comparison of intransal versus intravenous verapamil bioavailability," Int. J. Clin. Pharmacol. Ther. Toxicol., 1993, 31(2): 1 page.
Wenzel et al., "Dupilumab in persistent asthma with elevated eosinophil levels," N. Engl. J. Med., Jun. 2013, 368(26):2455-66.
Wioland et al., "CFTR, MDR1, and MRP1 immunolocalization in normal human nasal respiratory mucosa," J Histochem Cytochem, 2000, 48:1215-122.
Wisniewski et al., "Novel cytokines and cytokine-producing T cells in allergic disorders," Allergy Asthma Proc., 2011. 32(2):83-94.
Wolking et al., "Impact of Genetic Polymorphisms of ABCB1 (MDR.1, P-Glycoprotein) on Drug Disposition and Potential Clinical Implications: Update of the Literature," Clin Pharmacokinet, 2015, 54 (7):709-35, 27 pages.
Wu et al., "Altered microRNA Expression Profiles of Extracellular Vesicles in Nasal Mucus From Patients With Allergic Rhinitis," Allergy Asthma Immunol Res, 2015, 7:449-457.
Yakimchuk, "Exosomes: isolation and characterization methods and specific markers," Mater Methods, 2015, 5:1450-1453, 17 pages.
Yasun et al., "Enrichment and Detection of Rare Proteins with Aptamer-conjugated Gold Nanorods," Anal Chem, Jul. 2012, 84(14):6008-6015.
Zadeh et al., "Significance of eosinophilia in chronic rhinosinusitis," Am J Rhinol., 2002, 16(6):313-7.

\* cited by examiner

METHODS AND COMPOSITIONS TO TREAT AND DIAGNOSE DISEASES OR PATHOLOGIES ASSOCIATED WITH INFLAMMATION OF THE SINUSES AND NASAL CAVITY

CLAIM OF PRIORITY

This application is a National Stage entry of PCT/US2020/024476, filed on Mar 24, 2020, which claims the benefit of U.S. Provisional Application Ser. No. 62/823,233, filed on Mar. 25, 2019. The entire contents of the foregoing are incorporated herein by reference.

TECHNICAL FIELD

This invention relates to methods and compositions for the treatment of rhinosinusitis in a subject using topical verapamil.

BACKGROUND

Chronic Rhinosinusitis with Nasal Polyps(CRSwNP) is characterized by the presence of edematous polypoid mucosa and predominantly eosinophilic inflammation[1]. Corticosteroids remain the mainstay of treatment however they are non-targeted and may be associated with dose limiting side effects, even when given topically[2]. Consequently, the development of novel, cost effective, and targeted therapies represents a significant unmet need for patients with CRSwNP.

SUMMARY

Provided herein are methods for treating chronic rhinosinusitis in a subject. The methods include identifying a subject having chronic rhinosinusitis; and administering a composition comprising 5-150 mg verapamil to nasal passages and sinuses of the subject using a high volume, low pressure irrigation with normal saline, wherein the verapamil is administered locally to the subject's nasal passage and sinuses by irrigation with a high volume of saline.

In some embodiments, the subject has chronic rhinosinusitis with nasal polyps.

In some embodiments, the composition is administered one or two times a day, preferably wherein a dose of 10-300 mg/day is administered.

In some embodiments, the volume of saline is 100 or 150 ml up to 250 or 300 ml or 500 ml. In some embodiments, the volume of saline is 150 to 250 ml.

In some embodiments, 20 to 120 mg total verapamil per dose is administered, preferably wherein 40-240 mg verapamil is administered per day.

In some embodiments, the subject having chronic rhinosinusitis was identified by endoscopy.

In some embodiments, the subject having chronic rhinosinusitis was identified by computed tomography.

In some embodiments, the subject having chronic rhinosinusitis was identified by observing the subject's symptoms and duration of symptoms.

In some embodiments, the methods include monitoring the efficacy of the treatment by endoscopy or by computed tomography, or by observing the subject's symptoms and duration of symptoms.

In some embodiments, the methods include surgically removing any nasal polyps present in the subject and/or performing sinus surgery.

In some embodiments, the methods include administering one or more corticosteroids and/or one or more antibiotics.

In some embodiments, the corticosteroid is selected from dexamethasone, prednisone, prednisolone, triamcinolone, cortisol, budesonide, mometasone, fluticasone, flunisolide, and betamethasone.

In some embodiments, the antibiotic is selected from erythromycin, doxycycline, tetracycline, penicillin, beta-lactam, macrolide, fluoroquinolone, cephalosporin, and sulfonamide.

Also provided herein are kits for treating rhinosinusitis in a subject, said kits comprising components for a plurality of doses of a treatment for rhinosinusitis, wherein each dose comprises: a pharmaceutical composition comprising 5-150 mg verapamil; salts, preferably comprising sodium chloride and a buffering agent, optionally sodium bicarbonate; and a device for delivering a volume of the pharmaceutical composition to the subject's nasal passage and sinuses. In some embodiments, said device delivers the pharmaceutical composition to the subject's nasal passage and sinuses in a liquid form.

In some embodiments, the volume is 100 or 150 ml up to 250 or 300 ml or 500 ml. In some embodiments, the volume of saline is 100 to 250 ml In some embodiments, the salts comprise sufficient sodium chloride to provide a final concentration of 0.8-1%, preferably 0.9 percent sodium chloride, and buffering agent to provide a pH of 4.5 to 7.5.

In some embodiments, each dose further comprises one or both of a corticosteroid and an antibiotic.

In some embodiments, the kit also includes a corticosteroid and/or an antibiotic. In some embodiments, the corticosteroid is selected from dexamethasone, prednisone, prednisolone, triamcinolone, cortisol, budesonide, mometasone, fluticasone, flunisolide, and betamethasone. In some embodiments, the antibiotic is selected from erythromycin, doxycycline, tetracycline, penicillin, beta-lactam, macrolide, fluoroquinolone, cephalosporin, and sulfonamide.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

P-glycoprotein(P-gp), a membrane efflux pump, is overexpressed in CRSwNP[3][4] and regulates the secretion of Type 2 helper T cell(Th2) polarizing cytokines which promote polypoid inflammation[4], suggesting that P-gp may be a druggable target (see, e.g., WO2014/106021). P-gp is secreted into nasal mucus[5] via epithelial derived exosomes and can be used to predict disease severity and response to P-gp inhibitory therapy (see, e.g., WO2019139901).

Verapamil Hydrochloride(HCl) was one of the first inhibitors of P-gp to be identified. Recently, a double-blind, placebo-controlled, randomized clinical trial using oral Verapamil as a novel P-gp inhibitory therapy for CRSwNP (ClinicalTrials.gov #NCT02454608, IND Exemption# 126356)[6] was completed. The results found that the efficacy of Verapamil was commensurate with both oral steroids and biologic agents with no significant side effects. However, logistic regression analysis demonstrated that the dose utilized was subtherapeutic in patients with higher body mass indices (BMI) and elevated mucus total P-gp levels. These results indicated that while P-gp inhibition using Verapamil is a promising innovative therapy for CRSwNP, an alternative dosing and delivery method is necessary to achieve higher local concentrations while preventing possible cardiac side effects.

Previous human trials have studied the systemic effects of intranasal Verapamil HCl at both 1 mg [7] and 5 mg [8] per dose. Neither study demonstrated any significant side effects suggesting that topical intranasal Verapamil can be safely administered to subjects at total residual doses below 5 mg. Previous in vitro data [9][10] indicated that a minimal local dose of 0.03 mg of Verapamil HCl would be required to achieve inhibition of P-gp within the nasal epithelium. However, whether a safe and effective dose could be achieved using high volume nasal irrigation was unknown.

Provided herein are methods of using topical intranasal Verapamil HCl, administered twice daily (BID) at up to the Maximal Tolerated Dose (MTD). The results support the use of high volume, low pressure nasal irrigation to deliver verapamil to subjects with CRSwNP.

Verapamil

Verapamil hydrochloride is a calcium antagonist or slow-channel inhibitor. Verapamil Hydrochloride Injection, USP is a sterile, nonpyrogenic solution containing verapamil hydrochloride 2.5 mg/mL and sodium chloride 8.5 mg/mL in water for injection. The solution contains no bacteriostat or antimicrobial agent. May contain hydrochloric acid for pH adjustment; pH is 4.9 (4.0 to 6.5). The chemical name of Verapamil Hydrochloride, USP is benzeneacetonitrile, α-[3[{2-(3,4-dimethoxyphenypethyl)ethyl}methylamino] propyl]-3,4-dimethoxy-α-(1-methylethyl) hydrochloride.

Verapamil hydrochloride is a white or practically white crystalline powder. It is practically odorless and has a bitter taste. It is soluble in water; freely soluble in chloroform; sparingly soluble in alcohol; practically insoluble in ether.

Verapamil has the following structural formula:

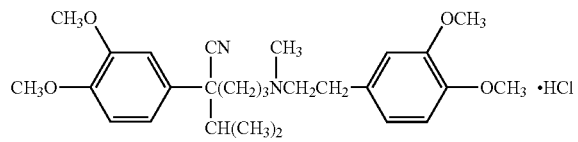

Molecular weight: 491.07, Molecular formula: C27H38N2O4.HCl[12,13]

While Verapamil is a cardioactive drug, it has a long history of use in the treatment of cluster headache in non-cardiac patients. It is considered the first-line prophylactic drug for cluster headache. It is usually well tolerated, although side effects include constipation and occasionally leg edema [14]. The usual starting dose is 80 mg 3 times a day, and the short-acting preparation is usually used. Verapamil has a short half-life (3-7 hours, although half-life may be up to 5-12 hours with chronic dosing) so dosing 3 times a day is necessary. Regular release verapamil tablets are usually used, as the slow release preparations do not seem to be reliable in terms of maintaining blood levels with longer dosing intervals. A concern with verapamil is its effects on atrioventricular conduction. It has been shown that approximately 19% of patients receiving verapamil for cluster headache develop electrocardiogram (EKG) abnormalities, although the great majority of these consist only of prolonged PR intervals, or right bundle branch blocks. However, about 4% can develop complete heart block with junctional rhythms [15]. Because of this, a slow increase in verapamil dosage has been recommended, with the dosage increased from the starting dose of 80 mg 3 times a day by 80 mg every 2 weeks [14] With this regimen, it takes 6 weeks to reach a dose of 480 mg daily. Although some patients will achieve effective prophylaxis at lower doses, patients with cluster headache may require verapamil doses more than this, and these are usually tolerated. Doses up to 640 mg daily are not uncommonly used, and higher doses have been reported to be effective and tolerated. A reasonable escalation regimen in cluster headaches is to start verapamil at 80 mg 3 times a day and to increase the verapamil dosage by 80 mg every week up to a dose of 480 mg daily. Above 480 mg, dosage increases of 80 mg every 2 weeks should be considered to ensure that the dosage is not higher than necessary to control the headaches. Although EKG changes can occur at lower doses, an EKG should certainly be done once a daily dose of 400 mg has been reached, and a week after each dosage increase above this level. A baseline EKG has also been recommended and periodic follow-up EKGs in patients on maintenance doses of verapamil, as arrhythmias may develop over time on stable verapamil doses [15]. Most patients tolerate even high-dose verapamil well [14]. In a study that reviewed 29 patients with cluster headache who were taking 720 mg or more of verapamil daily, 11 were found to have EKG abnormalities. However, 7 had only bradycardia, and 2 additional patients had only a prolonged PR interval. One patient had a second-degree heart block, and one had a third-degree heart block [16]. In total, 2 patients required discontinuation of verapamil, and one needed a dose reduction. Periodic EKGs are therefore important in patients on verapamil, particularly if they are taking a dose of over 480 mg[14].

Treatment Using Verapamil

In some embodiments, a subject having chronic rhinosinusitis (CRS) is identified and treated by administration to the subject an effective amount of verapamil.

CRSwNP is Chronic Rhinosinusitis with Nasal Polyps whereas the term Chronic Rhinosinutis (CRS) encompasses patients with and without nasal polyps. In some embodiments, the present methods are used to treat subjects with CRS without nasal polyps, as some patients with CRS but without polyps still have polyp-like inflammation. The subject having rhinosinusitis may be identified by one of skill in the art based on known methods, e.g., based on detection of the presence of symptoms, by endoscopy, or by computed tomography. The efficacy of the treatment may be monitored by methods known in the art, e.g., by monitoring symptoms, by endoscopy or computed tomography. Improvements of the subject include a better symptom score, e.g. a better SNOT-22 or VAS score; a reduction in inflammation or nasal polyp burden as revealed by endoscopy, e.g. a better Lund-Kennedy score; or a reduction in mucosal thickening or sinus opacification as revealed by computed tomography (CT), e.g. a better Lund-Mackay score. The 22-item Sinonasal Outcomes Test (SNOT-22) is a questionnaire encompassing 22 major symptoms on rhinosinusitis and nasal polyps, and serves as a valuable tool to measure the severity of a subject's symptoms and their impact on health-related quality of life (Quintanilla-Dieck, et al., International Forum of Allergy & Rhinology 2012; 2(6):437-443). The SNOT-22 assessed 12 nasal- and sinus-related symptoms (nasal blockage, loss of sense of taste and smell; need to blow nose, sneezing, runny nose, cough, postnasal discharge, thick nasal discharge, ear fullness, dizziness, ear pain, and facial pain/pressure) and 10 psychological and behavioral symptoms (difficulty falling asleep, waking up at night, lack of a good night's sleep, waking up tired, fatigue, reduced productivity, reduced concentration, frustrated/restless/irritable, sad, and embarrassed) with participants scoring each symptom on a scale of 0 (absent) to 5 (severe) on average for the last week, for a total score range of 0 to 100. The SNOT-22 score is the mean for the 22 scores (Piccirillo et al., Otolaryngol Head Neck Surg 2002; 126:41-47). The 10-symptom visual analog (VAS) scale is a questionnaire based on the major and minor symptom diagnostic criteria for CRS as described by the American Academy of Otolaryngology—Head and Neck Surgery TFR. The VAS assessed subject-reported severity of each of the following symptoms on average experienced during the prior week: nasal drainage of pus, nasal obstruction/congestion, impaired sense of smell, facial pressure/pain, headache, bad breath, weakness/fatigue, dental pain, ear fullness/pain, and cough (Ryan, et al., Laryngoscope 2011; 121:674-678). The Lund-Kennedy endoscopy scoring system quantifies the pathologic states of the nose and paranasal sinuses as assessed by nasal endoscopy, focusing on the presence of polyps, discharge, edema, scarring or adhesions, and crusting (Ryan, et al., 2011). The Lund Mackay CT scoring system is the most widely used CT grading system for chronic rhinosinusitis. This scoring system consists of a scale of 0-2 dependent on the absence (0), partial (1) or complete (2) opacification of the sinus system and the osteomeatal complex as assessed by CT imaging (Hopkins et al., Otolaryngology—Head and Neck Surgery 2007; 137:555-561).

In the present methods, a subject with chronic rhinosinusitis, e.g., CRSwNP, is treated with the P-gp inhibitor verapamil in an amount sufficient to inhibit P-gp function. The verapamil is administered locally to the subject's nasal passage and sinuses by irrigation with a high volume of saline, e.g., 100 or 150 ml up to 250 or 300 ml or 500 ml; in some embodiments, 150 to 240 or 250 ml saline is used. In some embodiments, the amount of drug administered is 5 mg, 10 mg, or 40 mg up to 100 mg, 120 mg or 150 mg, e.g., 5 to 150,10 to 120 mg, or 40 to 120 mg per dose, and a dose is administered, e.g., once, twice, or three times or more, per day. In some embodiments, the amount of drug administered is 10 mg, 20 mg, or 80 mg up to 120 mg, 240 mg or 300 mg, e.g., 10 to 300, 20 to 240 mg, or 80 to 240 mg total per day.

In some embodiments, a subject with rhinosinusitis is treated with verapamil in combination with other conventional treatments, e.g., drugs such as corticosteroids and/or antibiotics, to potentiate the effect of treatment. For example, verapamil may be used in combination with a corticosteroid selected from dexamethasone, prednisolone, triamcinolone, cortisol, prednisone, budesonide, mometasone, fluticasone, flunisolide, and betamethasone. In some embodiments, verapamil is used in combination with an antibiotic selected from macrolides, e.g., erythromycin; penicillins, e.g., amoxicillin , beta-lactam, ampicillin; tetracyclines, e.g., doxycycline, tetracycline; sulfonamides, e.g. mafenide, sulfacetamide; fluoroquinolones; and cephalosporins, e.g., ceftaroline fosamil, ceftobiprole. In some embodiments, verapamil is used in combination with a corticosteroid and an antibiotic.

In some embodiments, when a subject with rhinosinusitis has nasal polyps, surgical removal of such nasal polyps and/or sinus surgery can be performed in addition to administration of verapamil to the subject. Thus, a subject with rhinosinusitis may undergo both surgery and treatment with verapamil using the present methods.

Pharmaceutical Compositions, Dosage, Methods of Administration, Kits

The methods of treatment described herein also include the use of pharmaceutical compositions, which include verapamil as an active ingredient. In some embodiments the composition also includes one or more supplementary active compounds incorporated therein, e.g., one or more corticosteroids and/or one or more antibiotics. The corticosteroid can be, e.g., selected from dexamethasone, prednisone, prednisolone, triamcinolone, cortisol, budesonide, mometasone, fluticasone, flunisolide, or betamethasone. The antibiotic can be, e.g., selected from erythromycin, doxycycline, tetracycline, penicillin, beta-lactam, macrolide, fluoroquinolone, cephalosporin, and sulfonamide. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. The present methods include the use of high volume, low pressure nasal irrigation with saline comprising an effective amount of verapamil.

Methods of formulating suitable pharmaceutical compositions are known in the art, see, e.g., Remington: *The Science and Practice of Pharmacy,* 21st ed., 2005; and the books in the series *Drugs and the Pharmaceutical Sciences: a Series of Textbooks and Monographs* (Dekker, N.Y.).

The pharmaceutical compositions can be included in a container, pack, or dispenser together with instructions for administration.

In some embodiments, a kit for treating rhinosinusitis in a subject is provided. Such a kit comprises a pharmaceutical composition comprising an effective amount of verapamil, optionally a corticosteroid and/or an antibiotic, and a device for delivering the pharmaceutical composition to the subject's nasal passage and sinuses, such as a squeeze bottle. The verapamil (and optional corticosteroid and/or an antibiotic) can be provided in a concentrated form, and the kit can also include sufficient salts to provide an isotonic (normal saline) solution for comfortable nasal irrigation upon addition of water (e.g., distilled or other clean water, not necessarily sterile). In some embodiments, the salts comprise sodium chloride and a buffering agent, e.g., sodium bicarbonate, e.g., sufficient sodium chloride to provide a final concentration of 0.8-1%, e.g., 0.9 percent sodium chloride, and buffering agent to provide a pH of 4.5 to 7.

Each dose of the verapamil (and optional corticosteroid and/or an antibiotic) and salt can be provided in a single container or in multiple individual containers. The containers can be, e.g., a bottle, vial, ampoule, packet or sachet.

The kit can also include one or more viscosity enhancing agents, such as a cellulose polymer or polyethylene glycol (PEG); preservatives; and/or surfactants, which can be incorporated into, e.g. mixed in with, one or more of the verapamil (and optional corticosteroid and/or an antibiotic) and salt. See, e.g., US20180104253.

In addition, the kit can include a bottle, e.g., a reusable bottle, e.g., as known in the art (see also U.S. Pat. Nos. 1,603,758; 1,856,811; 3,847,145; 5,649,530; 6,328,718; 6,520,284; 6,736,792; 6,907,879; 8,162,921; US PGPUB 2006/0276743; 2009/0202665; 2008/0221507; WO 2006/051206; WO 2008/058160; and US2017/0128659, inter alia.

EXAMPLES

The invention is further described in the following examples, which do not limit the scope of the invention described in the claims.

Example 1

Double-Blind Placebo-Controlled Randomized Clinical Trial of Verapamil for Chronic Rhinosinusitis with Nasal Polyps We previously undertook a randomized, double-blind, placebo-controlled trial to test the efficacy of low dose oral Verapamil HCl, a known first generation P-gp inhibitor, for the treatment of CRSwNP [6]. While Verapamil is cardioactive, it is considered a first-line prophylactic drug for cluster headache and is well tolerated at 80 mg three times a day (TID) by otherwise healthy patients [14]. The findings demonstrated significant efficacy in both our primary and secondary endpoints with no significant side effects. The least squares mean (LSM) change between baseline and week 8 SNOT-22 score was 227.3 (95% CI, 242.56 to 212.05)in the verapamil group and 0.4 (95% CI, 214.85 to 15.66) in the placebo group, resulting in a final LSM difference of 227.7 between groups (95% CI, 249.36 to 26.05; P=0.01). Similarly, the final LSM difference in VAS score between groups was 237.97 (95% CI, 260.01 to 215.93; P=0.001). The LMS demonstrated a significant difference favoring the verapamil group with an absolute mean difference of 25.20 (95% CI, 29.66 to 20.74; P=0.02; intraclass correlation coefficient, 0.97). A significant reduction in total LKS was observed in the verapamil group compared with placebo at week 4, with an LSM difference of 22.8 between groups (95% CI, 24.63 to 20.98; P=0.003).

However, a linear regression analysis revealed two important relationships between baseline characteristics and efficacy. First, patients with elevated BMI had significantly lower improvements in SNOT-22(p=0.01). This is consistent with the use of a low dose of a relatively low potency inhibitor. The second is that patients with the highest total mucus P-gp levels experienced less benefit (p=0.01). This suggested that the mechanism of Verapamil is acting through P-gp inhibition and that patients with greater expression may need higher concentrations to achieve adequate pump suppression. While Verapamil HCl has significant potential for the treatment of CRSwNP through P-gp inhibition, higher doses must be achieved to extend the effect to patients with elevated BMIs and the highest levels of P-gp expression. As increasing oral dosing could result in cardiac side effects, topical delivery represents a promising alternative.

Example 2

Phase Ib Clinical Trial of Topical Verapamil HCl for Chronic Rhinosinusitis with Nasal Polyps This study evaluated the safety and tolerability of nasal delivery of Verapamil using a high volume, low pressure irrigation method. The phase IB study consisted of an accelerated titration, intrapatient dose escalation cohort, with double-dose step design. The initial single patient cohort will began using 10 mg Verapamil HCL dissolved in an irrigation bottle containing 240 mL buffered saline for nasal use (NeilMed Pharmaceuticals Inc, Santa Rosa, Calif.) BID for 1 week. Using this method it has been established that 97% of the irrigation volume functions as a carrier which is immediately lost through the nostrils and mouth yielding an approximately effective 3% residual dose of 0.3 mg which is retained within the nasal cavity [9]. The first dose was administered in the clinic with EKG and hemodynamic monitoring. Patients were instructed on the how to properly perform the irrigation using a pre-recorded video demonstration. If no first-course dose limiting toxicity (DLT, defined by the development of 2nd or 3rd degree heart block) was noted then patients were instructed to continue taking the current Verapamil rinse dose BID for 1 week. Dose escalation was planned to occur weekly in the absence of a single, any course, DLT or a second, any course, intermediate toxicity (IT, defined by a heart rate of <50, an asymptomatic BP reduction>30% from baseline or systolic BP<90mmHg, an asymptomatic MAP reduction>30% from baseline or MAP<55, an asymptomatic diastolic BP reduction>30% from baseline, and a Meltzer Compliance Grade>4[60]).

Each escalation represented a doubling of the residual dose 0.3-2.4 mg. At that point the residual dose escalated in 0.6 mg residual intervals for the rest of the trial up to a maximum of 3.6 mg total residual dose. These doses were derived from the pharmacokinetic analysis of our oral Verapamil trial results. If a single, any course, DLT or second, any course, IT occurs, two additional patients were planned to be recruited at that identified dose and Phase IB would revert to a standard 3+3 design. If any patient un-enrolled during dose escalation they were to be replaced to maintain 3 patient cohorts. The maximal administered dose (MAD) was considered the immediate preceding dose at which at least 2 DLTs or 4 ITs occurred or the predetermined MTD.

At the conclusion of the study, 8 patients signed consent. These 8 patients included 5 males and 3 females age 18-60, 7 Caucasian (4 M and 3 F) and 1 African-American (1 M). 1 female subject and 5 male subjects completed the study. 5 Caucasian, 1 African-American. The other 2 female subjects were found to be ineligible. Regarding the primary outcome measure, the MAD/MTD was determined to be 120 mg IV topical verapamil BID in 240 cc buffered normal saline with 0% dose limiting, intermediate, or mild toxicities at the MAD/MTD. Regarding adverse events 1 patient had a transient low heart rate during escalation which resolved at higher doses and 1 patient reported headache.

ARM 2: Phase 2

The Phase II study is an open label safety and efficacy expansion cohort using the MTD determined in the Phase IB arm. A total of 20 patients are administered the MTD of topical Verapamil HCl in a 240 mL buffered saline nasal rinse for 4 weeks BID. This sample size was calculated based on a power analysis derived from the results of our oral Verapamil trial. The first dose is administered in the clinic with EKG and hemodynamic monitoring. Patients are instructed on the how to properly perform the irrigation using a pre-recorded video demonstration. If no first-course DLT occurs then patients continue taking the topical Verapamil dose BID. Patients return for follow-up visits at 1 week and 4 weeks. Subjective and objective outcome measures are collected at each visit.

Statistical Analysis

The proposed sample size of 20 subjects for the Phase II expansion cohort was determined to detect, with an 80% power at a 5% type-1 error rate, a change of 15.9 points on the primary endpoint (ie. SNOT-22 score) between baseline and 4 weeks assuming a standard deviation of 24. This calculation was derived from the established MCID for the SNOT-22 of 8.9[11] and our oral Verapamil trial findings[6]. Analysis of efficacy will be based on an intention-to-treat population that will include all enrolled patients. A mixed-effect model with repeated measures approach will be used to independently analyze the change in the SNOT-22, VAS, and LKS. Linear regression models will be fitted to examine the interaction effect between baseline characteristics, whole mucus and exosomal P-gp concentrations, mucus and irrigant cytokine concentrations, and treatment on change in SNOT-22 while adjusting for the baseline SNOT-22 score.

Subject Inclusion Criteria

Age 18-80 years old ; Diagnosed with Chronic Rhinosinusitis with Nasal Polyps according to the EPOS 2012 consensus criteria; Post-operative with a Lund-Kennedy Poly score of <4; Baseline SNOT-22 Score≥30

Subject Exclusion Criteria

Patients with the following comorbidities: GI Hypomotility; Heart Failure; Liver Failure; Kidney Disease; Muscular Dystrophy; Pregnant or Nursing Females; Steroid Dependency; Hypertrophic Cardiomyopathy; Any Atrial or Ventricular arrhythmia (ie. Atrial fibrillation, atrial flutter, etc.); Resting Heart Rate less than 60 beats per minute; Baseline Systolic Blood Pressure less than 110 mmHg; Baseline Diastolic Blood Pressure less than 70 mmHg; Baseline Mean Arterial Pressure Less than 60 mmHg; PR interval less than 0.12 seconds Patients taking the following medications: Aspirin; Beta-blockers; Cimetidine(Tagamet); Clarithromycin(Biaxin); Cyclosporin; Digoxin; Disopyramide(Norpace); Diuretics; Erythromycin; Flecainide; HIV Protease Inhibitors(Indinavir, Nelfinavir, Ritonavir); Quinidine; Lithium; Pioglitazone; Rifampin; St Johns Wort Patients with cardiac or conduction abnormality picked up by screening EKG Patients with a Systolic BP<100, Patients with a MAP>65, Patients with a HR<65, Patients with a PR interval>200 ms, Post-op patients with surgery within 3 months prior to enrollment.

REFERENCES

1. Chin D, Harvey R J. Nasal polyposis: an inflammatory condition requiring effective anti-inflammatory treatment. Curr. Opin. Otolaryngol. Head Neck Surg. 2013; 21:23-30.
2. Poetker D M, Jakubowski L a, Lal D, Hwang P H, Wright E D, Smith TL. Oral corticosteroids in the management of adult chronic rhinosinusitis with and without nasal polyps: an evidence-based review with recommendations. Int. Forum Allergy Rhinol. 2013; 3:104-20. Available at: http://www.ncbi.nlm.nih.gov/pubmed/22887970.
3. Bleier BS, Article O. Regional expression of epithelial MDR1/P-glycoprotein in chronic rhinosinusitis with and without nasal polyposis. Int. Forum Allergy Rhinol. 2012; 2:122-5.
4. Bleier BS, Nocera AL, Iqbal H, et al. P-glycoprotein promotes epithelial T helper 2-associated cytokine secretion in chronic sinusitis with nasal polyps. Int. Forum Allergy Rhinol. 2014; 4:488-94.
5. Nocera A L, Meurer A T, Miyake M M, Sadow P M, Han X, Bleier B S. Secreted P-glycoprotein is a noninvasive biomarker of chronic rhinosinusitis. Laryngoscope 2016;
6. Miyake M M, Nocera A L, Levesque P, et al. Double-Blind Placebo-Controlled Randomized Clinical Trial of Verapamil for Chronic Rhinosinusitis with Nasal Polyps. J. Allergy Clin. Immunol. 2017;
7. Secher C, Brofeldt S, Mygind N. Intranasal verapamil in allergen-induced rhinitis. Allergy 1983; 38:565-70.
8. Watling S, Engelhardt J, Kandrotas R, et al. Comparison of intranasal versus intravenous verapamil bioavailability. Int. J. Clin. Pharmacol. Ther. Toxicol. 1993; 31:100-4.
9. Harvey R J, Debnath N, Srubiski A, Bleier B, Schlosser R I Fluid residuals and drug exposure in nasal irrigation. Otolaryngol.—Head Neck Surg. 2009; 141:757-761.
10. Sarangapani R, Teeguarden J G, Gentry P R, Clewell H J, Barton H a, Bogdanffy MS. Interspecies dose extrapolation for inhaled dimethyl sulfate: a PBPK model-based analysis using nasal cavity N7-methylguanine adducts. Inhal. Toxicol. 2004; 16:593-605.
11. Hopkins C, Gillett S, Slack R. Psychometric validity of the 22-item Sinonasal Outcome Test. Clin. . . . 2009; :447-454.
12. Verapamil Hydrocholride Injection, USP. Prescribing Information. Hospira, Inc. Lake Forest, IL. Revised March 2010
13. Verapamil Hydrochloride Injection. Safety Data Sheet. Hospira GEHS. Revised Jun. 2, 2014
14. Becker W. Cluster headache: conventional pharmacological management. Headache 2013; 53:1191-6. Available at: doi:10.1111/head0.12145.
15. Cohen A, Matharu M, Goadsby P. Electrocardiographic abnormalities in patients with cluster headache on verapamil therapy. Neurology 2007; 69:668-675. Available at: doi:10.1212/01.wnl.0000267319.18123.d3.
16. Lanteri-Minet M, Silhol F, Piano V, Donnet A. Cardiac safety in cluster headache patients using the very high dose of verapamil (>720 mg/day). J. Headache Pain 2011; 12:173-6. Available at: http://link. springer. com/article/10.1007/s10194-010-0289-x.
17. Kocharyan A, Feldman R, Singleton A, Han X, Bleier B S. P-glycoprotein inhibition promotes prednisone retention in human sinonasal polyp explants. Int. Forum Allergy Rhinol. 2014; 4:734-8.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating rhinosinusitis in a subject, having elevated body mass index and/or elevated mucus total P-gp levels, the method comprising:
   identifying that the subject has chronic rhinosinusitis; and
   administering a composition comprising 5-150 mg verapamil to nasal passages and sinuses of the subject using a high volume, low pressure irrigation with normal saline, wherein the verapamil is administered locally to the subject's nasal passage and sinuses by irrigation with a high volume of saline.

2. The method of claim 1, wherein the subject has chronic rhinosinusitis with nasal polyps.

3. The method of claim 1, wherein the composition is administered one or two times a day, wherein a dose of 10-300 mg/day is administered.

4. The method of claim 1, wherein the volume of saline is 100 to 500 ml.

5. The method of claim 4, wherein the volume of saline is 150 to 250 ml.

6. The method of claim 1, wherein 20 to 120 mg total verapamil per dose is administered, and wherein 40-240 mg verapamil is administered per day.

7. The method of claim 1, wherein the subject having rhinosinusitis was identified by endoscopy, computed tomography, or by observing the subject's symptoms and duration of symptoms.

8. The method of claim 1, further comprising monitoring the efficacy of the treatment by endoscopy, computed tomography, or by observing the subject's symptoms and duration of symptoms.

9. The method of claim 1, further comprising administering one or more corticosteroids and/or one or more antibiotics.

10. The method of claim 9, wherein the corticosteroid is selected from dexamethasone, prednisone, prednisolone, triamcinolone, cortisol, budesonide, mometasone, fluticasone, flunisolide, and betamethasone.

11. The method of claim 9, wherein the antibiotic is selected from erythromycin, doxycycline, tetracycline, penicillin, beta-lactam, macrolide, fluoroquinolone, cephalosporin, and sulfonamide.

12. A kit for treating rhinosinusitis in a subject having elevated body mass index and/or elevated mucus total P-gp levels, said kit comprising components for a plurality of doses of a treatment for rhinosinusitis, wherein each dose comprises:
   a pharmaceutical composition comprising 5-150 mg verapamil;
   salts, comprising sodium chloride and a buffering agent; and
   a device for delivering a volume of the pharmaceutical composition to the subject's nasal passage and sinuses.

13. The kit of claim 12, wherein said device delivers the pharmaceutical composition to the subject's nasal passage and sinuses in a liquid form.

14. The kit of claim 12, wherein the volume is 100 to 500 ml.

15. The kit of claim 14, wherein the volume of saline is 100 to 250 ml.

16. The kit of claim 12, wherein the salts comprise sufficient sodium chloride to provide a final concentration of 0.8-1%, sodium chloride, and buffering agent to provide a pH of 4.5 to 7.5.

17. The kit of claim 12, wherein each dose further comprises one or both of a corticosteroid and an antibiotic.

18. The kit of claim 12, further comprising a corticosteroid and/or an antibiotic.

19. The kit of claim 18, wherein the corticosteroid is selected from dexamethasone, prednisone, prednisolone, triamcinolone, cortisol, budesonide, mometasone, fluticasone, flunisolide, and betamethasone.

20. The kit of claim 18, wherein the antibiotic is selected from erythromycin, doxycycline, tetracycline, penicillin, beta-lactam, macrolide, fluoroquinolone, cephalosporin, and sulfonamide.

* * * * *